United States Patent [19]

Herring

[11] Patent Number: 5,286,849
[45] Date of Patent: Feb. 15, 1994

[54] PURIFICATION OF FACTOR IX

[75] Inventor: Steven W. Herring, San Dimas, Calif.

[73] Assignee: Alpha Therapeutic Corporation, Los Angeles, Calif.

[21] Appl. No.: 913,666

[22] Filed: Jul. 14, 1992

[51] Int. Cl.$^5$ .................. A61K 35/16; A61K 37/02; C07K 3/20
[52] U.S. Cl. .................................. 530/381; 530/384; 530/413; 530/417; 530/420; 530/427
[58] Field of Search ............... 530/381, 384, 413, 417, 530/420, 427

[56] References Cited

U.S. PATENT DOCUMENTS 4,725,673  1/1988  Herring .............................. 530/381

OTHER PUBLICATIONS

Pepper et al., "Chromatography of Human Prothrombin Complex on Dextran Sulphate Agarose," *Thrombosis Research*, II, 687–692 (1977).
Ahmad et al., "Rapid Purification of Factor IX, Factor X and Prothrombin by Immunoaffinity and Ion Exchange Chromatography," *Thromb. Res.*, 55, 121–133 (1989).
Tharakan et al., "Development of an Immunoaffinity Process for Factor IX Purification," *Vox Sang*, 58, 21–29 (1990).
Hrinda et al., "Preclinical Studies of a Monoclonal Antibody-Purified Factor IX, Mononine$^{TM}$," *Sem. in Hematol.*, 28, 6–14 (1991).
Kim et al., "Purified Factor IX Using Monoclonal Immunoaffinity Technique: Clinical Trials in Hemophilia B and Comparison to Prothrombin Complex Concentrates," *Blood*, 79, 568–575 (1992).
Bajaj et al., "A Simplified Procedure for Purification of Human Prothrombin, Factor IX and Factor X," *Prep. Biochem.*, 11, 397–412 (1981).
Andersson et al., "Purification and Characterization of Human Factor IX," *Thromb. Res.*, 7, 451–459 (1975).
Menache et al., "Coagulation Factor IX Concentrate: Method of Preparation and Assessment of Potential In Vivo Thrombogenicity in Animal Models," *Blood*, 64, 1220–1227 (1984).
T. Brodniewicz-Proba, "Human Plasma Fractionation and the Impact of New Technologies on the Use and Quality of Plasma-derived Products," *Blood Reviews*, 5, 245–257 (1991).

*Primary Examiner*—Howard E. Schain
*Assistant Examiner*—P. Lynn Touzeau
*Attorney, Agent, or Firm*—Christie, Parker & Hale

[57] ABSTRACT

The present invention relates to a process for purifying Factor IX from an impure protein fraction containing Factor IX. The purification process comprises the steps of adding a solvent and a detergent to an impure protein fraction and incubating the solvent/detergent protein solution to inactivate any viral contaminants. Factor IX is purified from the solvent/detergent protein solution by chromatography on a sulfated polysaccharide resin without first removing the solvent and detergent prior to the purification on the sulfated polysaccharide resin. The Factor IX, purified by the process has a specific activity of at least 85 units/mg.

12 Claims, No Drawings

PURIFICATION OF FACTOR IX

FIELD OF THE INVENTION

This invention relates to a method useful for separation of Factor IX from an impure protein fraction which includes Factor IX.

BACKGROUND OF THE INVENTION

The initiation of blood clotting is by two different, yet similar, molecular mechanisms called the intrinsic and extrinsic coagulation pathways, or cascades. The intrinsic pathway involves factors that are normally found in the blood. The extrinsic pathway involves tissue factors in addition to blood components. In each of the reaction steps of the two cascades, a proteinase converts an inactive zymogen into its enzymically active form. In the last step of the cascade, which is the same in both the intrinsic and extrinsic pathways, inactive prothrombin is converted to thrombin, which in turn catalyzes the conversion of soluble fibrinogen into insoluble fibrin.

Factor IX participates in the cascade of events that lead to blood coagulation. Specifically, Factor IX, when activated by the action of Factors $XI_a$ or $VIII_1$, activates Factor X to $X_a$. Factor $X_a$ in turn activates Factor II (prothrombin) to Factor $II_a$ (thrombin). The activated Factor II then activates fibrinogen to form the fibrin polymers of the blood clot. A deficiency in the activity of any of the factors involved in blood clotting leads to an inability of the blood to clot properly or to longer-than-normal clotting times. For example, Factor IX is absent or deficient in patients who have a condition identified as "Hemophilia B." Thus, the blood of Hemophilia B patients does not clot properly. Factor IX is administered to Hemophilia B patients to provide sufficient Factor IX, to return the clotting ability of their blood to as close to normal as possible.

Commercially available Factor IX concentrates frequently include other blood factors in addition to Factor IX. For example, some such preparations comprise the prothrombin complex which includes Factors II, V, and X in addition to Factor IX.

The occurrence of thrombotic complications, such as deep vein thrombosis, disseminated intravascular coagulation, and pulmonary embolism have been reported in patients treated with prothrombin complex concentrates or in Factor IX preparations that are contaminated with Factor II and/or Factor X. These complications are frequently seen in premature infants, in patients with poor liver function, and in surgery patients. Such complications have also been observed in Hemophilia A patients receiving prothrombin complex concentrate as a Factor VIII inhibitor bypassing agent.

The thrombogenic component of prothrombin complex concentrates has been attributed most often to either activated factors, coagulant active phospholipid, or zymogen overload. Zymogen overload may be the basis of disseminated intravascular coagulation in surgical situations where patients receive large and repetitive doses of prothrombin complex concentrates. In such cases, a buildup of zymogens in the circulation, particularly of Factors II and X, is likely to occur due to their relatively long half-life in relation to Factor IX.

The thrombotic complications associated with the use of prothrombin complex make it desirable to provide a Factor IX concentrate, essentially free of other proteins, for use in treating Hemophilia B patients Various methods for enhancing the purity of Factor IX concentrates have been reported. For example, processes for producing concentrates of Factor IX, essentially free of prothrombin, and of Factor X by use of affinity chromatography on a sulfated dextran resin have been disclosed (D. Menache et al., "Coagulation Factor IX Concentrate: Method of Preparation and Assessment of Potential In Vivo Thrombogenicity in Animal Models", *Blood,* 64. 1220–1227 [1984]). Factor IX has been purified by affinity chromatography on a heparin-sepharose resin (L-O. Andersson et al., "Purification and Characterization of Human Factor IX", *Thrombosis Research,* 7, 451–459 [1975]). Factors IX and X have been separated by using a process which includes heparin-agarose chromatographic techniques (S. P. Bajaj et al., "A Simplified Procedure For Purification of Human Prothrombin Factor IX and Factor X", Preoarative Biochemistry, 11, 397–412 [1981]). Procedures are a)so known in the art for separating Factor IX by affinity chromatography on a dextran sulfate-sepharose gel.

While Factor IX can be separated on sepharose (agarose gels) in the laboratory, the use of agarose gels for large-scale separations has been found to be unsatisfactory. When the agarose gels are packed into commercial-size columns, they compress to an undesirable extent and thereby inhibit flow of liquids through the column. This problem has been overcome by the use of dextran sulfate silica resin, as described in U.S. Pat. No. 4,725,673 to Herring, incorporated herein by this reference. While this purification method is desirable in that the silica gel results in higher flow rates and, therefore, faster purification procedures, it uses a heat treatment to inactivate any viral contaminants that may be present in the human blood-derived protein preparations The heat treatment results in denaturation of a portion of the Factor IX which can lead to low specific-activity Factor IX preparations.

In addition to the above methods, purification of Factor IX has been performed using immunoaffinity and ion-exchange chromatography (S.S. Ahmad et al., "Rapid Purification of Factor IX, Factor X and Prothrombin by Immunoaffinity and Ion Exchange Chromatography", *Thromb. Res.,* 55, 121–133 [1989]), which has resulted in specific-activities as high as 269 units/mg, for Factor IX. While immunoaffinity methods lead to high specific-activity preparations, the necessity to prepare monoclonal antibodies against the proteins to be purified adds a significant cost to the purification procedure.

It is therefore desirable to provide, at a relatively low cost, a process for the purification of Factor IX which yields a high specific-activity Factor IX preparation that is safe for use in humans.

SUMMARY OF THE INVENTION

The present invention relates to a process for purifying Factor IX from an impure protein fraction containing Factor IX. The purification process comprises the steps of providing an aqueous solution of the impure protein fraction, adding a solvent and a detergent to the impure protein fraction to form a solvent/detergent protein solution, incubating the solvent/detergent protein solution to inactivate any viral contaminants present in the solvent/detergent protein solution and further purifying the Factor IX by chromatography on a sulfated polysaccharide resin.

The Factor IX, purified by the above described process, has a specific activity of at least 85 units/mg.

DETAILED DESCRIPTION

The present invention is directed at a method of purifying Factor IX from an impure protein fraction. The purification method comprises a method of inactivating any viral or other contaminants, that may be present in the blood, which does not lead to extensive denaturation of the proteins to be purified Previous methods have relied on heat treatment to inactivate contaminants. Such heat treatment also leads to denaturation of a portion of the Factor IX. The denaturation results in a loss of Factor IX activity, but this inactivated Factor IX may co-purify with the active Factor IX, resulting in a final product which comprises both active and inactive Factor IX. The presence of the inactive Factor IX leads to a lower specific-activity than would result from a preparation which comprised only, or greater levels of, Factor IX. The method of the present invention incorporates a solvent/detergent inactivation step, rather than heat inactivation, to reduce the amount of denatured Factor IX produced during the purification procedure.

The process provided in accordance with practice of principles of this invention relates to the separation of Factor IX from an impure protein fraction. As used herein, an "impure protein fraction" means a protein fraction which includes one or more protein(s) in addition to Factor IX.

Although the process of the invention is described below with reference to separation of Factor IX from human plasma, the process is contemplated to be useful as well for separating Factor IX from other sources, such as from recombinant organisms engineered to express the desired protein.

SEPARATION OF PROTHROMBIN COMPLEX PROTEINS FROM HUMAN PLASMA

Prothrombin complex proteins are separated from human plasma that has been collected and tested according to procedures approved by the U.S. Food and Drug Administration. The plasma is initially frozen at a temperature of about $-20°$ C. The plasma is then thawed at 0° C. to 5° C. to allow cryoprecipitation to occur. The resulting plasma-cryoprecipitate mixture is pooled and centrifuged to remove the cryoprecipitate. The pooled AHF-poor plasma is then weighed, brought to 0° C. to 5° C., and electrodialyzed to reduce the plasma sodium concentration from its original value to between 85 and 105 mM. The dialyzed AHF-poor plasma is then adjusted to about a neutral pH by the addition of acetic acid.

The prothrombin complex factors contained in the pH-adjusted AHF-poor plasma are adsorbed onto regenerated DEAE (diethyl aminoethyl) cellulose. The DEAE cellulose and the plasma are mixed for approximately 30 minutes, and the DEAE cellulose is then collected by centrifugation. The DEAE cellulose-adsorbed prothrombin complex is washed with a wash buffer comprising about 0.03M sodium phosphate and about 0.03M sodium citrate at a pH of about 6.8. The wash is discarded.

The washed DEAE cellulose-adsorbed prothrombin complex is then removed from the centrifuge and suspended in a wash buffer. The resulting suspension is then poured into a column, and the eluate from the column is discarded. The DEAE cellulose is then washed with a wash buffer, and this wash is also discarded. The prothrombin complex factors are then eluted by washing the column with an eluting buffer comprising 0.03M sodium phosphate, 0.03M sodium citrate, and 0.2M sodium chloride at a pH of about 6.8. The eluate is collected, and the prothrombin complex-containing fractions are pooled and collected in a bulk solution. Appropriate tests of the collected prothrombin-complex fractions are performed and, after the pH of the bulk solution is adjusted to about neutral, the solution is filtered through a sterile bacteria-retentive cartridge or membrane, to thereby form a bulk solution of filtered prothrombin complex. The bulk solution of filtered prothrombin complex is then frozen until needed for processing or is immediately processed further.

Solvent/Detergent (S/D) Inactivation of Viral Contaminants

In order to inactivate any viral or other contamination present in the blood-derived protein fraction, about one kilogram (kg) of bulk solution of filtered prothrombin complex is mixed with about 0.1 kg of a mixture comprising about 3% tri-(n)butyl phosphate and about 10% (wt/wt) monooleate (also known as polysorbate 80 and Tween 80). The solution is adjusted to a pH of about 6.8 and incubated, with mixing, at about 27° C. for about 6 to about 7 hours. At the end of the incubation, the S/D-treated prothrombin complex is diluted to about 2 mg of protein/ml with a solution comprising about 0.02M sodium citrate and about 0.05M sodium chloride at a pH of about 7.3 to about 7.5.

Separation of Factor IX from Prothrombin Complex by Barium Chloride Precipitation To separate the Factor IX from the prothrombin complex, a volume of about 0.5M to about 2M barium chloride solution, sufficient to precipitate Factor IX, is added to the dilute S/D-treated prothrombin complex solution. The precipitate, which comprises Factor IX, is collected and dissolved in a solution of about 0.2 to about 0.6M (ethylenedinitrilo)tetraacetic acid (EDTA) and diafiltered against a low-sodium buffer (0–0.2M NaCl, in a buffered solution at a pH of between about 6 to about 9 to remove barium and EDTA and to obtain a desirably-low sodium concentration for further processing. A suitable buffer for the diafiltration comprises about 0.02M sodium citrate at a pH of about 6.6 to about 7 and about 0.05M NaCl.

While in the practice of the present invention it is preferred that a barium chloride precipitation step is included in the purification, the barium chloride may be omitted if desired In such a case the Factor IX would be purified by applying the S/D-treated prothrombin complex directly to a sulfated polysaccharide resin as described below.

Separation of Factor IX from Barium Chloride Precipitate

The diafiltered barium chloride precipitate solution is then further purified on a sulfated polysaccharide resin, such as that described in the U.S. Pat. No. 4,725,673 patent to Herring, which is incorporated herein by reference. It is preferable in the practice of the present invention that the sulfated polysaccharide is attached to a hard resin, such as, silica, methacrylate-glycerol copolymer, polystyrenedivinyl benzene, polyvinyl copolymer, or any of the other hard resins that are known in the art. The use of hard resins is preferred, since they do not compress during the purification process.

A quantity of about 3.8 to about 6 liters of sulfated polysaccharide resin is packed into a column for each kg of diafiltered barium chloride precipitate solution to be purified.

The diafiltered barium chloride precipitate solution is applied to the sulfated polysaccharide resin so that the Factor IX contained in the solution is adsorbed onto the resin. After the adsorption step is completed, the Factor IX adsorbed on the resin is washed with a volume of a wash buffer (about 0.02M sodium citrate, at a pH of about 6.6 to about 7.0, and about 0.05M NaCl) approximately equal to at least five times the volume of resin in the column. Factor IX is then eluted from the resin with a linear salt (sodium chloride) gradient from about 0.05M NaCl to about 0.6 NaCl. When the salt gradient reaches a concentration of about 0.4M, the eluate contains essentially only Factor IX. At the completion of the salt gradient, the column is further eluted by washing with a wash buffer containing the maximum level of sodium chloride used in the gradient, e.g., 0.6M. The Factor IX-containing eluate is pooled and diafiltered to reduce the sodium concentration to desired target levels. The pooled Factor IX fractions may be filtered and frozen for later processing, or they may be processed immediately, if desired. If frozen, the samples are thawed and combined with other pooled fractions, where desired, and the pH is adjusted to about 6.8, if necessary.

After the purification of the Factor IX on the sulfated polysaccharide resin the solvent/detergent viral inactivation agents have been removed from the Factor IX fraction and no additional steps are required to separate these "contaminants" from the final protein product.

Further Purification of Factor IX

The pooled Factor IX-containing fractions are then reapplied to a sulfated polysaccharide resin packed into a column. In this case, about 0.57 to about 2.35 kg of sulfate polysaccharide resin is used for each about-five kg of Factor IX eluted from the first sulfated polysaccharide resin. After the Factor IX-containing solution is applied to the sulfated polysaccharide resin, the resin is washed with a wash buffer (about 0.02M sodium citrate and about 0.05M sodium chloride at a pH of about 6.6 to about 7), as described above. Factor IX is eluted from the column with a solution comprising about 0.02M sodium citrate and about 0.6M sodium chloride, at a pH of about 6.6 to about 7.

The Factor IX-containing fractions are pooled and diafiltered to target Factor IX activity and sodium concentration levels. Heparin and dextrose may be added to the Factor IX containing fractions if desired. The Factor IX-containing solution is then sterile-filtered, as described above, to form Factor IX sterile bulk.

The Factor IX sterile bulk is sampled for sterility and Factor IX activity. Fill volume is calculated based upon Factor IX activity. The sterile bulk is filled into clean, sterilized vials, then frozen and dried under vacuum, stoppered, and sealed. The freeze-dried final-container Factor IX is then tested by quality control. When test results are within all applicable specifications, quality control releases the lot.

EXAMPLE 1

Purification of Factor IX Using a Solvent/Detergent Inactivation Step

In one example of practice of this invention for the purification of Factor IX, the Factor IX contained in cryoprecipitate poor plasma was adsorbed onto DEAE-cellulose which had been previously equilibrated with 0.03M sodium phosphate and 0.03M sodium citrate at a pH of 6.8. The DEAE cellulose and plasma were mixed for approximately 30 min., and the DEAE cellulose collected by centrifugation was washed with 0.03M sodium phosphate and 0.03M sodium citrate at a pH of 6.8. The wash was discarded.

The washed DEAE cellulose was suspended in 0.03M sodium phosphate and 0.03M sodium citrate, at a pH of 6.8, and poured into a column. The eluate was discarded. The DEAE cellulose was washed with 0.03M sodium phosphate and 0.03M sodium citrate, at a pH of 6.8, and this wash was also discarded. The Factor IX was eluted by washing the DEAE cellulose with 0.03M sodium phosphate, 0.03M sodium citrate, at a pH of 6.8, and 0.2M NaCl. The eluate was collected, and the Factor IX-containing fraction was pooled and collected into a bulk solution. The solution was filtered through a sterile bacteria-retentive cartridge.

36.6 kg of bulk solution of filtered prothrombin complex was mixed with about 3.9 kg of a mixture comprising 3% tri-(n)butyl phosphate and 0% (wt/wt) monooleate (also known as polysorbate 80 and Tween 80). The solution was adjusted to a pH of 6.8 and incubated, with mixing, at 27° C. for 6 hours At the end of the incubation, the S/D-treated prothrombin complex was diluted to about 1.5 mg of protein/ml with 244 kg of solution comprising 0.02M sodium citrate and 0.05M sodium chloride, at a pH of about 7.4.

46.6 kg of 1.0M barium chloride solution (4° C.) was added over the course of 2 hours, and the mixture was stirred for one additional hour. The mixture was kept at between 0° C. and 4° C. during the addition of barium chloride and during mixing. After mixing, the solution was centrifuged in a Sharples centrifuge, keeping the flow rate through the centrifuge at between 0.2 and 0.6 per liter per min., and the temperature of the solution at between 0° C. and 4° C. Approximately 1.6 kg of barium chloride precipitate was collected in this manner.

To the barium chloride precipitate, about 58 kg of a 0.4M EDTA solution, at 20° C. to 25° C., was added to dissolve the precipitate, and the precipitate was filtered through a Millipore TP cartridge filter to remove particulate. After filtration, the solution was passed through a Millipore Pellicon concentrator and was concentrated to between 1/5 and 1/10 of its original volume. The concentrated solution was then diluted to its original volume, with 0.02M sodium citrate and 0.05M NaCl. The concentration and dilution steps were repeated six more times, at which point the conductivity of the solution was approximately equal to that of the solution containing 0.02M sodium citrate 0.05M sodium chloride. After final dilution, the weight of the diafiltered material was 70 kg. The redissolved precipitate contained Factor IX.

70 kg of the diafiltered Factor IX containing material was applied, at a flow rate of about 260 ml/min., to a 36 cm×37 cm Moduline chromatographic column containing dextran sulfate silica resin, equilibrated with wash buffer (0.02M sodium citrate and 0.05M sodium chloride, pH 6.8). Subsequently, 323 kg of wash buffer was passed through the column.

Immediately after the column was washed as described above, a 228-liter, linear salt gradient from 0.05M NaCl to 0.5M NaCl in 0.02M sodium citrate, pH 6.8, was applied to the column at a flow rate of 1 liter/min. 5 liter aliquots of the column eluate were collected during the gradient, and every third fraction was assayed to determine its Factor IX activity. After completion of the gradient, an additional 157 liters of the solution containing 0.02M sodium citrate, pH 6.8, and 0.5M NaCl, was applied to the column, and 5-liter aliquots of the eluate were collected and assayed for Factor IX activity.

The Factor IX containing fractions were pooled and the pooled material (42 liter) was concentrated about five-fold by passage through a Millipore Pellicon concentrator. The sodium concentration was adjusted to 110 meq/liter by addition of wash buffer and the sodium adjusted Factor IX pool was reduced to a volume of 35 liters. This material was applied at a flow rate of 90 ml/min to 12.1 liters of dextran sulfate silica, packed in a Moduline chromatographic column and equilibrated with wash buffer. The chromatographic medium was then washed with 96 kg of wash buffer. The chromatographic medium was then eluted with 96 liter of a solution comprising 0.02M sodium citrate, pH 6.8 and 0.6M NaCl. 4.75-liter fractions were collected and assayed for Factor IX activity. The Factor IX containing fractions were pooled and the pooled material (37 liter) was assayed for Factor IX activity and $A_{280}$.

The results of these assays are shown in Table I.

TABLE I

|  | Specific-Activity of Factor IX (Units/$A_{280}$) |
| --- | --- |
| Plasma fraction[1] | 3.3 |
| Eluate[2] | 180 |

[1]Prothrombin complex
[2]Eluate from the two dextran sulfate chromatography steps.

The purity (specific-activity) of Factor IX was increased 55 fold by sequential chromatography on two dextran sulfate silica columns.

EXAMPLE 2

Purification of Factor IX Using a Heat Inactivation Step

The process described in Example 1 was repeated, except that heat inactivation was used in place of the solvent detergent step. The bulk solution of filtered prothrombin complex was filtered through a sterile bacteria-retentive cartridge, then lyophilized. The lyophilized powder was viral-inactivated by suspension in n-heptane and heating at 60° C. for 20 hours. Heptane was removed by drying.

About 2.04 kg of dried powder was reconstituted with approximately 64.5 kg of cold water for injection. The reconstituted powder was diluted with 266.6 kg of 0.02M sodium citrate, pH 7.4, and 0.25M NaCl at 4° C., and mixed for 20 min. at 2° C. to 4° C. The solution was then subjected to barium chloride precipitation, and the precipitate was filtered through a Millipore TP cartridge filter to remove particulates. After filtration the material was diafiltered as described Example 1. The diafiltered material was applied at a flow rate of about 120 ml/min. to a 18 cm×98 cm Moduline chromatographic column containing dextran sulfate silica resin, equilibrated with wash buffer (0.02M sodium citrate and 0.05M sodium chloride, pH 6.8). Subsequently, 25 kg of wash buffer was passed through the column.

Immediately after the column was washed as described above, a 150-liter, linear salt gradient from 0.05M NaCl to 0.5M NaCl in 0.02M sodium citrate, pH 6.8, was applied to the column at a flow rate of 1 liter/min. 3.5 liter aliquots of the column eluate were collected during the gradient, and every third fraction was assayed to determine its Factor IX activity. After completion of the gradient, an additional 50 liters of the solution containing 0.02M sodium citrate, pH 6.8, and 0.5M NaCl, was applied to the column, and 3.5-liter aliquots of the eluate were collected and assayed for Factor IX activity. The Factor IX containing fractions were pooled and the pooled material was concentrated by ultrafiltration and assayed for Factor IX activity and $A_{280}$.

The results are summarized in Table II.

TABLE II

|  | Specific-Activity of Factor IX (Units/$A_{280}$) |
| --- | --- |
| Plasma fraction[1] | 3.42 |
| Concentrate[2] | 62.7 |

[1]Prothrombin complex
[2]Concentrated eluate from the dextran sulfate chromatography step.

The results indicate that the specific-activity of the Factor IX is 62.7 units/$A_{280}$.

The above description of preferred embodiments of processes for separating Factor IX from impure protein fractions containing Factor IX is for illustrative purposes. Variations will be apparent to those skilled in the art. Therefore, the present invention is not intended to be limited to the particular embodiments described above. Also the invention disclosed may be practiced in the absence of any element which is not specifically disclosed in the specification. The scope of the invention is defined in the following claims.

What is claimed is:

1. A process for purifying Factor IX from an impure protein fraction containing Factor IX, the process comprising the steps of:

providing an aqueous solution of the impure protein fraction;

adding a solvent and a detergent to the impure protein fraction to form a solvent/detergent protein solution;

incubating the solvent/detergent protein solution to inactive any viral contaminants present in the solvent/detergent protein solution; and further purifying Factor IX by applying the incubated solvent/detergent solution to a sulfated polyusaccharide resin wherein the solvent/detergent is removed from the Factor IX fraction by chromatography on the sulfated polysaccharide resin.

2. The process according to claim 1 wherein the detergent comprises monooleate.

3. The process according to claim 1 wherein the detergent is present at a concentration of about 10% (wt/wt).

4. The process according to claim 1 wherein the solvent comprises tri-(n)butyl phosphate.

5. The process according to claim 1 wherein the solvent is present at a concentration of about 3% (wt/wt).

6. The process according to claim 1 wherein the solvent/detergent protein fraction is incubated for about 6 hours at about 27° C.

7. The process according to claim 1 wherein the sulfated polysaccharide is heparin.

8. The process according to claim 1 wherein the sulfated polysaccharide is dermatan sulfate.

9. The process according to claim 1 wherein the sulfated polysaccharide is heparin sulfate.

10. The process according to claim 1 wherein the sulfated polysaccharide is dextran sulfate.

11. A process for purifying Factor IX from an impure protein fraction containing Factor IX, the process comprising the steps of:

providing an aqueous solution of the impure protein fraction;

adding a solvent and a detergent to the impure protein fraction to form a solvent/detergent protein solution;

incubating the solvent/detergent protein solution to inactive any viral contaminants present in the solvent/detergent protein solution;

precipitating Factor IX from the incubated solution; and further purifying Factor IX from the redissolved Factor IX precipitate by chromatography on a sulfated polysaccharide resin wherein the solvent/detergent is removed from the Factor IX fraction by chromatography on the sulfated polysaccharide resin.

12. The process according to claim 11 wherein the Factor IX precipitant comprises barium chloride.

* * * * *

UNITED STATES PATENT AND TRADEMARK OFFICE
CERTIFICATE OF CORRECTION

PATENT NO. : 5,286,849
DATED : February 15, 1994
INVENTOR(S) : Steven W. Herring It is certified that error appears in the above-indentified patent and that said Letters Patent is hereby corrected as shown below:

Column 1, line 26, change "$VII_1$" to -- $VII_a$ --.

Column 2, line 2, after "patients" insert a period.
Column 2, line 20, change "Preoarative" to
   -- Preparative --.
Column 2, line 21, change "a)so" to -- also --.
Column 2, line 38, after "preparations" insert a period.

Column 3, line 12, after "purified" insert a period.

Column 4, line 25, change "0.1" to -- 0.11 --.
Column 4, line 55, after "desired" insert a period.

Column 6, line 30, change "0%" to -- 10% --.
Column 6, line 33, after "hours" insert a period.
Column 6, line 46, change "1.6" to -- 11.6 --.

Column 7, line 16, change "42 liter" to
   -- 142 liter --.
Column 7, line 64, after "described" insert -- in --.
Column 7, line 66, before "18 cm" change "a"
   to -- an --.

UNITED STATES PATENT AND TRADEMARK OFFICE
CERTIFICATE OF CORRECTION

PATENT NO. : 5,286,849
DATED : February 15, 1994
INVENTOR(S) : Steven W. Herring It is certified that error appears in the above-indentified patent and that said Letters Patent is hereby corrected as shown below:

Column 8, line 50, change "inactive" to
        -- inactivate --.
Column 8, line 55, change "polusaccharide" to
        -- polysaccharide --.

Column 10, line 5, change "inactive" to
        -- inactivate --.
Column 10, line 7, after "incubated" insert
        -- solvent/detergent protein --.
Column 10, line 8, delete "and" and insert therefor
        -- redissolving the factor IX precipitate in
           an aqueous solution; and --.

Signed and Sealed this

Thirteenth Day of September, 1994

Attest:

BRUCE LEHMAN

*Attesting Officer*      *Commissioner of Patents and Trademarks*